United States Patent [19]

Jungheim et al.

[11] Patent Number: 4,826,992
[45] Date of Patent: May 2, 1989

[54] 2,3-(DIHYDRO) BICYCLIC PYRAZOLIDINONES

[75] Inventors: Louis N. Jungheim; Sandra K. Sigmund, both of Indianapolis, Ind.

[73] Assignee: Eli Lilly and Company, Indianapolis, Ind.

[21] Appl. No.: 934,054

[22] Filed: Nov. 24, 1986

Related U.S. Application Data

[63] Continuation of Ser. No. 728,716, Apr. 30, 1985, abandoned.

[51] Int. Cl.⁴ .......................................... C07D 231/00
[52] U.S. Cl. .................................. 548/359; 544/182; 544/235; 544/238; 544/295; 544/296; 544/316; 544/357; 544/405; 546/199; 546/271; 548/110; 548/125; 548/131; 548/132; 548/136; 548/137; 548/187; 548/204; 548/229; 548/251; 548/253; 548/255

[58] Field of Search ............... 544/182, 235, 238, 295, 544/296, 316, 357, 405; 546/277, 279, 199; 548/100, 125, 131, 132, 136, 137, 187, 204, 229, 251, 253, 255, 110, 359

[56] References Cited

U.S. PATENT DOCUMENTS 4,128,425 12/1978 Greenwald .
4,512,924 4/1985 Attwood et al. .

OTHER PUBLICATIONS

H. Dorn and A. Otto, Angew. Chem. Int. Ed. Engl., 7, pp. 214–215 (1968).

Primary Examiner—Robert W. Ramsuer
Attorney, Agent, or Firm—William B. Scanlon; Paul C. Steinhardt; Leroy Whitaker

[57] ABSTRACT

2,3-(Dihydro) bicyclic pyrazolidinones are intermediates for bicyclic pyrazolidinone antimicrobials.

6 Claims, No Drawings

2,3-(DIHYDRO) BICYCLIC PYRAZOLIDINONES

This application is a continuation, of application Ser. No. 728,716, filed 4/30/85, now abandoned.

SUMMARY OF THE INVENTION

The invention is directed to intermediate compounds of the formula

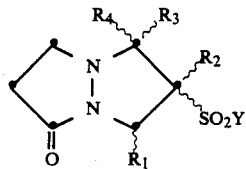

wherein $R_1$, $R_2$, $R_3$, $R_4$ and Y have the meanings defined below. The above compounds are intermediates in the synthesis of bicyclic pyrazolidinone antimicrobials.

DETAILED DESCRIPTION OF THE INVENTION

I. THE INVENTION IN GENERAL; DEFINITION OF TERMS

The present invention embraces compounds of the Formula I:

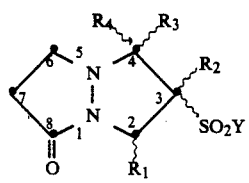

I

The ring system of compound Formula I is a 1,5-diazabicyclo[3.3.0]octane ring, often referred to in this specification as a "saturated bicyclic pyrazolidinone". The numbering system for the ring system is denoted in Formula I.

The undulating lines connecting $R_3$ and $R_4$ to position 4, $R_1$ to position 2, and $R_2$ and $SO_2$ to position 3 of the ring system indicate that the stereochemistry at positions 2, 3 and 4 could be independently in the R or S configuration. Furthermore, the Formula represents compounds of the invention in various percentage mixtures of the possible enantiomeric and diastereomeric mixtures.

In the above Formula I:
either $R_1$ or $R_2$ is hydrogen, $C_1$ to $C_6$ alkyl, $C_1$ to $C_6$ substituted alkyl, perfluoro $C_2$ to $C_4$ alkyl, $C_7$ to $C_{12}$ alkylaryl, $C_7$ to $C_{12}$ substituted alkylaryl, phenyl, substituted phenyl or cyano;
a group of the formula

—$CX_3$ wherein X is fluoro, chloro, bromo or iodo;
a group of the formula

—S—$R_5$ wherein Z is 0, 1 or 2 and $R_5$ is $C_1$ to $C_6$ alkyl, $C_1$ to $C_6$ substituted alkyl, phenyl, substituted phenyl, $C_7$ to $C_{12}$ alkylaryl, $C_7$ to $C_{12}$ substituted alkylaryl or a heterocyclic ring; a group of the formula

—$COR_6$ wherein $R_6$ is hydrogen, $C_1$ to $C_6$ alkyl, $C_1$ to $C_6$ substituted alkyl, perfluoro $C_2$ to $C_4$ alkyl, trihalomethyl, $C_7$ to $C_{12}$ alkylaryl, $C_7$ to $C_{12}$ substituted alkylaryl, phenyl or substituted phenyl;
a group of the formula

—$COOR_7$ wherein $R_7$ is hydrogen, an organic or inorganic cation, $C_1$ to $C_6$ alkyl, $C_1$ to $C_6$ substituted alkyl, $C_7$ to $C_{12}$ alkylaryl, $C_7$ to $C_{12}$ substituted alkylaryl, phenyl, substituted phenyl, a carboxy protecting group, or a non-toxic, metabolically-labile ester-forming group;
or a group of the formula
—$CH_2$-S-Heterocyclic ring;
and the other of $R_1$ or $R_2$ is a group of the formula

—$COOR_8$ wherein $R_8$ is hydrogen, an organic or inorganic cation, a carboxy protecting group, or a non-toxic, meta-bolically-labile ester-forming group; and
$R_3$ and $R_4$ are the same or different and are hydrogen, $C_1$ to $C_6$ alkyl, $C_1$ to $C_6$ substituted alkyl, $C_7$ to $C_{12}$ alkylaryl, $C_7$ to $C_{12}$ substituted alkylaryl, phenyl, substituted phenyl or a group of the formula

—$COOR_9$ wherein $R_9$ has the same definition as $R_7$;
Y is $C_1$ to $C_6$ alkyl, $C_1$ to $C_6$ substituted alkyl, phenyl, substituted phenyl, $C_7$ to $C_{12}$ alkylaryl or $C_7$ to $C_{12}$ substituted alkylaryl;
or a pharmaceutically-acceptable salt thereof.

In the above Formula I, the term "$C_1$ to $C_6$ alkyl" denotes such radicals as methyl, ethyl, n-propyl, isopropyl, n-butyl, sec-butyl, tert-butyl, amyl, tert-amyl, hexyl and the like. The preferred "$C_1$ to $C_6$ alkyl" group is methyl.

The term "$C_1$ to $C_6$ substituted alkyl" denotes the above $C_1$ to $C_6$ alkyl groups that are substituted by one or two halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy groups. The substituted alkyl groups may be substituted once or twice with the same or with different substituents.

Examples of the above substituted alkyl groups include the cyanomethyl, nitromethyl, hydroxymethyl, trityloxymethyl, propionyloxymethyl, aminomethyl, carboxymethyl, allyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, 6-hydroxyhexyl, 2,4-dichloro(n-butyl), 2-amino(iso-propyl), 2-carbamoyloxyethyl and the like. A preferred group of examples within the above "$C_1$ to $C_6$ substituted alkyl" group includes the substituted methyl group, in other words, a methyl group substituted by the same substituents as the "$C_1$ to $C_6$ substituted alkyl" group. Examples of the substituted methyl group include groups such as hydroxymethyl, protected hydroxymethyl, (e.g., tetrahydropyranyloxymethyl)-,acetoxymethyl, carbamoyloxymethyl, chloromethyl, bromomethyl and iodomethyl.

The term "$C_1$ to $C_4$ alkoxy" as used herein denotes groups such as methoxy, ethoxy, n-propoxy, isopropoxy, n-butoxy, t-butoxy and like groups. Similarly, the term "$C_1$ to $C_7$ acyloxy" denotes herein groups such as formyloxy, acetoxy, propionyloxy, butyryloxy, pentanoyloxy, hexanoyloxy, heptanoyloxy, and the like.

Examples of the term "perfluoro $C_2$ to $C_4$ alkyl" include perfluoroethyl, perfluoro n-propyl, perfluoro iso-propyl, perfluoro n-butyl, perfluoro sec-butyl and the like.

The term "substituted phenyl" specifies a phenyl group substituted with one or two moieties chosen from the group consiting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl or methylsulfonylamino.

Examples of the term "substituted phenyl" include a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono- or di(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy4-methoxyphenyl and the like; 3- or 4- trifluoromethylphenyl, a mono- or dicarboxyphenyl or (protected carboxy) phenyl group such as 4-carboxyphenyl or 2,4-di(-protected carboxy)phenyl, a mono- or di(hydroxymethyl)phenyl or (protected hydroxymethyl)phenyl such as 3-(protected hydroxymethyl)phenyl or 3,4-di(hydroxymethyl)phenyl, a mono- or di(aminomethyl)phenyl or (protected aminomethyl)phenyl such as 2-(aminomethyl)phenyl or 2,4-(protected aminomethyl)-phenyl, or a mono- or di(methylsulfonylamino)phenyl such as 3-(methylsulfonylamino)phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(methylsulfonylamino)phenyl groups.

The terms "halo" and "halogen" refer to fluoro, chloro, bromo or iodo.

The term "trihalomethyl" denotes trifluoromethyl, trichloromethyl, tribromomethyl or triiodomethyl.

The term "$C_7$ to $C_{12}$ alkylaryl" denotes a $C_1$ to $C_6$ alkyl group substituted at any position by a phenyl ring. Examples of such a group include phenylmethyl (benzyl), 2-phenylethyl, 3-phenyl-(n-propyl), 4-phenylhexyl, 3-phenyl-(n-amyl), 3-phenyl-(sec-butyl) and the like. A preferred group is the benzyl group.

The term "$C_7$ to $C_{12}$ substituted alkylaryl" denotes a $C_7$ to $C_{12}$ substituted alkylaryl group substituted on the $C_1$ to $C_6$ alkyl portion with one or two groups chosen from halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy; and/or the phenyl group may be substituted with 1 or 2 groups chosen from halogen, hydroxy, protected hydroxy, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or a methylsulfonylamino group. As before, when either the $C_1$ to $C_6$ alkyl portion or the phenyl portion or both are disubstituted, the substituents can be the same or different.

Examples of the term "$C_7$ to $C_{12}$ substituted alkylaryl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6methoxyphenyl)-3-carboxy(n-hexyl), 5-(4-aminomethyl phenyl)-3-(aminomethyl)(n-pentyl), and the like.

The term "organic or inorganic cation" refers to counter-ions for the carboxylate anion of a carboxylate salt. The counter-ions are chosen from the alkali and alkaline earth metals, such as lithium, sodium, potassium, barium and calcium; ammonium; and organic cations such as dibenzylammonium, benzylammonium, 2-hydroxyethylammonium, bis(2-hydroxyethyl)ammonium, phenylethylbenzylammonium, dibenzylethylenediammonium, and like cations. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amine group is referred to by this term. A preferred cation for the carboxylate anion is the sodium cation.

The term "pharmaceutically acceptable salt" encompasses those salts that form with the carboxylate anions and includes the organic and inorganic cations discussed above. Furthermore, the term includes salts that form by standard acid-base reactions with basic groups (such as amino groups) and organic or inorganic acids. Such acids include hydrochloric, sulfuric, phosphoric, acetic, succinic, citric, lactic, maleic, fumaric, palmitic, cholic, pamoic, mucic, D-glutamic, d-camphoric, glutaric, phthalic, tartaric, lauric, stearic, salicyclic, methanesulfonic, benzenesulfonic, sorbic, picric, benzoic, cinnamic and like acids.

The compounds of Formula I may also exist as solvates and hydrates. Thus, the compounds may crystallize with, for example, waters of hydration, or one, a number of, or any fraction thereof of molecules of the mother liquor solvent. The solvates and hydrates of such compounds are included within the scope of this invention.

The terms "carboxy-protecting group" and "protected carboxy" as used in the specification refer to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(tri-methylsilylmethyl)prop-1-en-3-yl, and like moieties. The species of carboxy-protecting group employed is not critical so long as the derivatized carboxylic acid is stable to the condition of subsequent reaction(s) on other positions of the saturated bicyclic pyrazolidinone intermediates or the unsaturated bicyclic pyrazolidinone final products and can be removed at the appropriate point without disrupting the remainder of the intermediate or final product molecule. In particular, it is important not to subject the carboxy-protected saturated bicyclic pyrazolidinone intermediates or the unsaturated bicyclic pyrazolidinone final products to strong nucleophilic bases or reductive conditions employing highly activated metal catalysts such as Raney nickel. (Such harsh removal conditions are also to be avoided when removing amino-protecting groups and hydroxy-protecting groups, discussed below.) A preferred carboxylic acid protecting group is the allyl group. Similar carboxy-protecting groups used in the cephalosporin, penicillin and peptide arts can also be used to protect a carboxy group substituents of the bicyclic pyrazolidinones. Further examples of these groups are found in E. Haslam, "Protective Groups in Organic Chemistry" J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The terms "protected hydroxy" and "hydroxy-protecting group" refer to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, hoxytrityl, benzyl, allyl, trimethylsilyl, 4,4',4"-trimethoxytrityl, benzyl allyl trimethysilyl, (t-butyl)dimethylsilyl and 2,2,2-trichloroethoxycarbonyl groups and the like.

The species of hydroxy-protecting groups is not critical so long as the derivatized hydroxyl group is stable to the conditions of subsequent reaction(s) and can be removed at the appropriate point without disrupting the remainder of the saturated bicyclic pyrazolidinone intermediates or the bicyclic pyrazolidinone final products.

Further examples of hydroxy-protecting groups are described by C. B. Reese and E. Haslam, "Protective Groups in Organic Chemistry", J. G. W. McOmie, Ed., Plenum Press, New York, N.Y., 1973, Chapters 3 and 4, respectively, and T. W. Greene, "Protective Groups in Organic Synthesis", John Wiley and Sons, New York, N.Y., 1981, Chapters 2 and 3. Some preferred hydroxy protecting groups are the trityl group and the tetrahydropyranyl group.

The terms "amino-protecting group" and "protected amino" as used in the specification refer to substituents of the amino group commonly employed to block or protect the amino functionality while carrying out reactions at other functional groups on the compound. Examples of such amino protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcychexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl) ethoxycarbonyl, allyloxycarbonyl, 1-(trimethylsilyl-methyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like, the benzoylmethylsulfonyl group, the 2-(nitro)-phenylsulfenyl group, the diphenylphosphine oxide group and like amino-protecting groups. The species of amino-protecting group employed is not critical so long as the derivatized amino group is stable to the condition of subsequent reaction(s) on other positions of the saturated bicyclic pyrazolidinone intermediates and the unsaturated bicyclic pyrazolidinone final products and can be removed at the appropriate point without disrupting the remainder of the molecule. Preferred amino-protecting groups are the allyloxycarbonyl, the t-butoxycarbonyl and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7.

The term "non-toxic, metabolically-labile ester-forming group" refers to those biologically active ester forms which induce increased blood levels and prolong the efficacy of the corresponding non-esterified forms of the compounds. Such ester groups include the lower alkoxymethyl groups, for example, methoxymethyl, ethoxymethyl, iso-propoxymethyl and the like; the α-($C_1$ to $C_4$)alkoxyethyl groups, for example methoxyethyl, ethoxyethyl, propoxyethyl, iso-propoxyethyl, and the like; the 2-oxo-1,3-dioxolen-4-ylmethyl groups, such as 5-methyl-2-oxo-1,3-dioxolen-4-ylmethyl, 5-phenyl-2-oxo-1,3-dioxolen-4-ylmethyl, and the like; the $C_1$ to $C_3$ alkylthiomethyl groups, for example methylthiomethyl, ethylthiomethyl, iso-propylthiomethyl, and the like; the acyloxymethyl groups, for example pivaloyloxymethyl, α-acetoxymethyl, and the like; the ethoxycarbonyl-1-methyl group; the α-acyloxy-α-substituted methyl groups, for example α-acetoxyethyl, the 3-phthalidyl or 5,6-dimethylphthalidyl groups, the 1-($C_1$ to $C_4$ alkyloxycarbonyloxy)eth-1-yl groups such as the 1-(ethoxycarbonyloxy)eth-1-yl group; and the 1-($C_1$ to $C_4$ alkylaminocarbonyloxy)eth-1-yl groups such as the 1-(methylaminocarbonyloxy)eth-1-yl group.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated or partially unsaturated, with fully unsaturated rings being preferred.

Furthermore, the above optionally substituted five-membered or six-membered rings can optionally be fused to a aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic ring": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo1,5-b]-pyridazinyl and purinyl, as well as benzo-fused derivatives, for example benzoxazolyl, benzthiazolyl, benzimidazolyl and indolyl.

A preferred group of examples of the above heterocyclic rings, when $R_1$ or $R_2$ is a heterocyclic thiomethyl group, are 5-membered ring systems containing a sulfur or oxygen atom and one to three nitrogen atoms. Examples of such preferred groups include thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl and 1,2,4-oxadiazol-5-yl. A group of further preferred examples of 5-membered ring systems with 2 to 4 nitrogen atoms include imidazolyl, preferably imidazol-2-yl, triazolyl, preferably 1,3,4-triazol-5-yl, 1,2,3-triazol-5-yl and 1,2,4-triazol-5-yl, and tetrazolyl, preferably 1H-tetrazol-5-yl. A preferred group of examples of benzo-fused derivatives are, in particular, benzoxazol-2-yl, benzthiazol-2-yl, benzimidazol-2-yl and indol-2-yl.

Further specific examples of the above heterocyclic ring systems forming part of a heterocyclic thiomethyl group are 6-membered ring systems containing one to three nitrogen atoms. Such examples include pyridyl, such as pyrid-2-yl, pyrid-3-yl and pyrid-4-yl, pyrimidyl, preferably pyrimid-2-yl and pyrimid-4-yl, triazinyl, preferably 1,3,4-triazin-2-yl and 1,3,5-triazin-4-yl, pyridazinyl, in particular pyridazin-3-yl, and pyrazinyl. The pyridyl, pyrimid-2-yl, pyrimid-4-yl, pyridazinyl and the 1,3,4-triazin-2-yl radicals, the pyridine N-oxides and pyridazine N-oxides, are a preferred group.

The substituents for the optionally substituted heterocyclic ring systems, and further examples of the 5- and 6- membered ring systems discussed above, are found in W. Dückheimer et al., U.S. Pat. No. 4,278,793, issued July 14, 1981, columns 9 through 21 and columns 33 through 188, herein incorporated by reference. (In columns 33 through 188, the substituents under the heading "A" are examples of "heterocyclic ring" when the ring is a part of heterocyclic thiomethyl group.)

A particularly preferred group of examples of the term "heterocyclic ring", when the ring is part of a heterocyclic thiomethyl group, is 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-methyl-1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl1,2,3-triazol-5-yl, pyrid-2-yl N-oxide, 6-methoxy-2-(N-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-as-triazin-3-yl, 2,5-dihydro-5-oxo-6-hydroxy-as-triazin-3-yl sodium salt, 2,5-dihydro-5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]-pyridazin-6-yl, and 8-aminotetrazolo[1,5-b]pyridazin6-yl.

A most preferred group of examples of the term "heterocyclic ring" when the term is used in conjunction with a heterocyclic thiomethyl group are 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, IH-tetrazol-5-yl, 1-methyl-1H-tetrazol-5-yl, 1-(1-(dimethylamino)eth-2-yl)-1H-etrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

In the above Formula I, when $R_1$ or $R_2$ is a group of the formula

wherein $R_5$ is a heterocyclic group, examples of such groups are 1,3-thiazol-2-ylthio, 4-(carboxymethyl)-5-methyl-1,3-thiazol-2-ylthio, 4-(carboxymethyl)-5-methyl-1,3-thiazol-2-ylthio sodium salt, 1,2,4-thiadiazol-5ylthio, 3-methyl-1,2,4-thiadiazol-5-ylthio, 1,3,4-triazol-5-ylthio, 2-methyl-1,3,4-triazol-5-ylthio, 2-hydroxy- 1,3,4-triazol-5-ylthio, 2-(carboxy)-4-methyl-1,3,4-triazol-5-ylthio sodium salt, 2-(carboxy)-4-methyl-1,3,4-triazol-5-ylthio, 1,3-oxazol-2-ylthio, 1,3,4-oxadiazol-5-ylthio, 2-methyl-1,3,4-oxadiazol-5ylthio, 2-(hydroxymethyl)-1,3,4-oxadiazol-5-ylthio, 1,2,4-oxadiazol-5-ylthio, 1,2,4-oxadiazol-5-ylthio, 1,3,4-thiadiazol-5-ylthio, 2-methyl-1,3,4-thiadiazol-5-ylthio, 2-thiol-1,3,4-thiadiazol-5-ylthio, 2-(methylthio)-1,3,4-thiadiazol-5-ylthio, 2-amino-1,3,4-thiadiazol-5-ylthio, 1H-tetrazol-5-ylthio, 1-methyl-1H-tetrazol-5-ylthio, 1-(1-(dimethylamino)eth-2-ylthio)-1H-tetrazol-5-ylthio, 1-(carboxymethyl)-1H-tetrazol-5ylthio, 1-(carboxymethyl)-1H-tetrazol-5-ylthio sodium salt, 1-(methylsulfonic acid)-1H-tetrazol-5-ylthio, 1-(methylsulfonic acid)-1H-tetrazol-5-ylthio sodium salt, 2-methyl-1H-tetrazol-5-ylthio, 2-methyl-1,2,3-triazol-5-ylthio, 1-methyl-1,2,3-triazol-5-ylthio, pyrid-2-methyl-1,2,3-triazol-5-ylthio, 4-methyl-1,2,3-triazol-5-ylthio, pyrid-2-ylthio N-oxide, 6-methoxy-2-(N-oxide)-pyridaz-3ylthio, 6-hydroxypyridaz-3-ylthio, 1-methylpyrid-2-ylthio, 1-methylpyrid-4-ylthio, 2-hydroxypyrimid-4-ylthio, 1,4,5,6-tetrahydro-5,6-dioxo-4-methyl-as-triazin-3ylthio, 1,4,5,6-tetrahydro-4-(2-formylmethyl)-5,6-dioxo-as-triazin-3-ylthio, 2,5-dihydro-5-oxo-6-hydroxy-as-triazin-3-ylthio, 2,5-dihydro-5-oxo-6-hydroxy-as-triazin-3-ylthio sodium salt, 2,5-dihydro-5-oxo-6-hydroxy-2-methyl-as-triazin-3-ylthio sodium salt, 2,5-dihydro-5-oxo-6-hydroxy-2-methyl-as-triazin-3-ylthio, 2,5-dihydro-5-oxo-6-methoxy-2-methyl-as-triazin-3-ylthio, 2,5-dihydro-5-oxo-as-triazin-3-ylthio, 2,5-dihydro-5-oxo-2-methyl-as-triazin-3-ylthio, 2,5-dihydro-5-oxo-2,6-dimethyl-as-triazin-3-ylthio, tetrazolo[1,5-b]pyridazin6-ylthio, and 8-aminotetrazolo[1,5-b]pyridazin-6-ylthio; the corresponding sulfoxides and sulfones of the above heterocyclic thio groups, and the like.

Examples of the above group when $R_5$ is other than a heterocyclic group include $C_1$ to $C_6$ alkylthio groups such as methylthio, ethylthio, (sec-butyl)thio, (t-amyl)thio and (n-hexyl)thio, $C_7$ to $C_{12}$ alkylphenylthio groups such as 2-phenylpropylthio, benzylthio, 1-phenyl-(n-amyl)thio and 4-phenyl(n-butyl)thio; $C_1$ to $C_6$ substituted alkylthio groups such as cyanomethylthio, 2-hydroxyethylthio, 2-nitropropylthio, 2-carbamoyl(sec-butyl)thio, 5-chloroamylthio, 4-carboxyamylthio, 6-carbamoyloxyhexyl thio, 2-methoxyethylthio, isopropoxy(t-butyl)thio, 2-aminoethylthio, 2,5-dihydroxyamylthio, 3,3-dibromo(n-butyl)thio, 3-chloro-2-iodopropylthio and 4-acetoxy-6fluorohexylthio; $C_7$ to $C_{12}$ substituted alkylphenylthio groups such as 3-(3,4-diiodophenyl)propylthio, 1-(3-chloro-4-fluorophenyl)ethylthio, 6-(4-cyanophenyl)-hexylthio, 3-phenyl-1-chloro(sec-butyl)thio, 2-phenyl2-hydroxyethylthio, 5-phenyl-2-hydroxyamylthio, 2-(3- nitrophenyl)-3-ethoxypropylthio, 5,6-dihydroxy-2-(4- ethyl-2-hydroxyphenyl)hexylthio and 5-carbamoyl-3- nitro-2-(2,4-dimethoxyphenyl)amylthio; phenylthio, and (substituted phenyl)thio groups, and the corresponding sulfoxide and sulfone analogs thereof.

Examples of the (substituted phenyl)thio groups represented by $R_5$ include groups such as 4-chlorophenylthio, 2,6-dichlorophenylthio, 2,5-dichlorophenylthio, 3,4-dichlorophenylthio, 3-chlorophenylthio, 3-bromophenylthio, 4-bromophenylthio, 3,4-dibromophenylthio, 3-chloro4-fluorophenylthio, 2-fluorophenylthio, 4-hydroxyphenylthio, 3-hydroxyphenylthio, 2,4-dihydroxyphenylthio, 3or 4-nitrophenylthio, 4-cyanophenylthio, 4-methylphenylthio, 2,4-dimethylphenylthio, 2-methylphenylthio, 4-(isopropyl)phenylthio, 4-ethylphenylthio, 3-(n-propyl)phenylthio, 2,6-dimethoxyphenylthio, 4-methoxyphenylthio, 3-ethoxyphenylthio, 4-(iso-propoxy)phenylthio, 4-(t-butoxy)phenylthio, 3-ethoxy-4-methoxyphenylthio, a 3- or 4-(trifluoromethyl)phenylthio, 4-carboxyphenylthio, 2,4-di(protected carboxy)phenylthio, 3-(protected hydroxymethyl)phenylthio, 3,4-di(hydroxymethyl)phenylthio, 2-(aminomethyl)phenylthio, 2,4-di(protected aminomethyl)phenylthio, 3-(methylsulfonylamino)phenylthio, 3-methyl-4-hydroxyphenylthio, 3-chloro-4-hydroxyphenylthio, 2-methoxy-4-bromophenylthio, 4-ethyl-2hydroxyphenylthio, 3-hydroxy-4-nitrophenylthio, 2- hydroxy-4-chlorophenylthio and the corresponding sulfoxide and sulfone analogs thereof.

A preferred group of examples of the group

include: 4-(carboxymethyl)-5-methyl-1,3-thiazol-2-ylthio, 4-(carboxymethyl)-5-methyl-1,3-thiazol-2-ylthio sodium salt, 1,3,4-triazol-5-ylthio, 2-methyl-1,3,4-triazol-5ylthio, 1H-tetrazol-5-ylthio, 1-methyl-1H-tetrazol-5-ylthio, 1-(1-(dimethylamino)eth-2-ylthio)-1H-tetrazol-5-ylthio, 1-(carboxymethyl)-1H-tetrazol-5-ylthio, 1-(carboxymethyl)-1H-tetrazol-5-ylthio sodium salt, 1-(methylsulfonic acid)-1H-tetrazol-5-ylthio, 1-(methylsulfonic acid)-1H-tetrazol-5-ylthio sodium salt, 1,2,3-triazol-5-ylthio, 1,4,5,6-tetrahydro-5,6-dioxo-4-methyl-as-triazin-3-ylthio, 1,4,5,6-tetrahydro-4-(formylmethyl)5,6-dioxo-as-triazin-3-ylthio, 2,5-dihydro-5-oxo-6-hydroxy-2-methyl-as-triazin-3-ylthio sodium salt, 2,5-dihydro-5-oxo-6-hydroxy-2-methyl-as-triazin-3-ylthio, tetrazolo[1,5-b]pyridazin-6-ylthio, 8-aminotetrazolo[1,5-b]pyridazin-6-ylthio, methylthio, ethylthio, phenylthio, phenylsulfonyl, methylsulfonyl, methylsulfoxide, and phenylsulfoxide.

In the above Formula I, $R_1$ or $R_2$ can be an acyl group of the formula

Examples of such a group include when $R_6$ is: hydrogen (the formyl group); $C_1$ to $C_6$ alkyl, such as acetyl, sec-butylcarbonyl, t-amylcarbonyl and the like; $C_1$ to $C_6$ substituted alkyl, such as (3-cyanopropyl)carbonyl, 4,5-dichloroamylcarbonyl, 2-carboxy-1-nitroethylcarbonyl and the like; phenyl (the benzoyl group); substituted phenyl, for example, 4-methoxybenzoyl, 2,4-dimethylbenzoyl, 3-nitrobenzoyl, 4-trifluoromethylbenzoyl, 2,4-di(alkyloxycarbonyl)benzoyl, 2-(aminomethyl)benzoyl, 3-hydroxy-4-nitrobenzoyl, and the like; $C_7$ to $C_{12}$ alkylaryl, such phenylmethylcarbonyl, 2-phenylethylcarbonyl, phenyl(t-butyl)carbonyl, 3-phenylamylcarbonyl and the like; trihalomethyl, such as trifluoroacetyl, trichloroacetyl, tribromoacetyl or triiodoacetyl; $C_7$ to $C_{12}$ substituted alkylaryl, such as 3-(3,4-diiodophenyl)-propylcarbonyl, 1-(3-chloro-4-fluorophenyl)ethylcarbonyl, 6-(4-cyanophenyl)hexylcarbonyl, 3-phenyl-1-chloro(sec-butyl)carbonyl, 2-phenyl-2-hydroxyethylcarbonyl, 5-phenyl-2-hydroxyamylcarbonyl, 2-(3-nitrophenyl)-3-ethoxypropylcarbonyl, 5,6-dihydroxy-2-(4-ethyl-2-hydroxyphenyl)hexylcarbonyl, 5-carbamoyl-3-nitro-2-(2,4-dimethoxyphenyl)amylcarbonyl and the like; or perfluoro $C_2$ to $C_4$ alkyl, such as perfluoropropionyl, perfluorobutyryl, perfluoropentanoyl, and the like.

A preferred group of examples of the acyl group formed with $R_6$ is the acetyl, benzoyl, trifluoroacetyl, trichloroacetyl, tribromoacetyl, and triiodoacetyl groups.

When $R_1$ or $R_2$ in the above Formula I is a carboxyl group of the formula $$-COOR_7$$

examples include groups when $R_7$ is: $C_1$ to $C_6$ alkyl, such as ethoxycarbonyl, sec-butoxycarbonyl, t-amyloxy-carbonyl and the like; $C_1$ to $C_6$ substituted alkyl, such as (3-cyanopropyloxy)carbonyl, 4,5-dichloroamyloxycarbonyl, 2-carboxy-1-nitroethoxycarbonyl and the like; phenyl (the phenoxycarbonyl group); substituted phenyl, for example, 4-methoxyphenoxycarbonyl, 2,4-dimethylphenoxycarbonyl, 3-nitrophenoxycarbonyl, 4-trifluoromethylphenoxycarbonyl, 2,4-di(methoxycarbonyl)phenoxycarbonyl, 2-(aminomethyl)phenoxycarbonyl, 3-hydroxy-4-nitrophenoxycarbonyl, and the like; $C_7$ to $C_{12}$ alkylaryl, such benzyloxycarbonyl, 2-phenylethoxycarbonyl, phenyl(t-butoxy)carbonyl, 3-phenylamyloxycarbonyl and the like; trihalomethyl, such as trifluoromethoxycarbonyl, trichloromethoxycarbonyl, tribromomethoxycarbonyl or triiodomethoxycarbonyl; or $C_7$ to $C_{12}$ substituted alkylaryl, such as 3-(3,4-diiodophenyl)propoxycarbonyl, 1-(3- chloro-4-fluorophenyl)ethoxycarbonyl, 6-(4-cyanophenyl)hexyloxycarbonyl, 3-phenyl-1-chloro(sec-butoxy)carbonyl, 2-phenyl-2-hydroxyethoxycarbonyl, 5-phenyl-2-hydroxyamyloxycarbonyl, 2-(3-nitrophenyl)-3-ethoxypropoxycarbonyl, 5,6-dihydroxy-2-(4-ethyl-2-hydroxyphenyl)hexyloxycarbonyl and 5-carbamoyl-3-nitro-4-(2,4-dimethoxyphenyl)amyloxycarbonyl and the like.

Further examples of the above —$COOR_7$ group are when $R_7$ is: an organic or inorganic cation, such ammonium carboxylate, procaine carboxylate, (phenylethylbenzylammonium)carboxylate, phenylglycine carboxylate, lysine carboxylate, lithium carboxylate, potassium carboxylate, sodium carboxylate and the like; a carboxy protecting group, such as allyl carboxylate, p-methoxybenzyl carboxylate, di-(4-methoxy)benzhydryl carboxylate, benzhydryl carboxylate, 2,2,2-trichloroethyl carboxylate, trimethylsilyl carboxylate, (t-butyl)-dimethylsilyl carboxylate, β-(trimethylsilyl)ethyl carboxylate, trityl carboxylate, 4,4',4"-trimethoxytrityl carboxylate, p-toluenesulfonylethyl carboxylate, and the like; a nontoxic, metabolically-labile ester-forming group, such as methoxymethyl carboxylate, 5-methyl-2-oxo-1,3-dioxolen-4-ylmethyl carboxylate, ethylthiomethyl carboxylate, pivaloyloxymethyl carboxylate, 3-phthalidyl carboxylate, 1-(ethoxycarbonyloxy)-eth-1-yl carboxylate, 1-(methylaminocarbonyloxy)eth-1-yl carboxylate, and the like.

A preferred group of examples of the carboxy group —$COOR_7$ is when $R_7$ is a $C_1$ to $C_6$ alkyl group, a carboxy protecting group, hydrogen or an organic or inorganic cation. An especially preferred group of examples of the above carboxy group is when $R_7$ is methyl, ethyl, hydrogen, allyl, benzyl, or sodium.

Examples of the group —$COOR_9$ are given above in conjunction with the carboxy group —$COOR_7$.

A preferred group of examples of the group —$COOR_9$ occurs when $R_9$ is a $C_1$ to $C_6$ alkyl group. An especially preferred carboxyl group of the above formula is ethyl carboxylate.

In the above Formula I, $R_1$ and $R_2$ can be a carboxy group of the formula $$-COOR_8$$

Examples of this group includes groups wherein $R_8$ is: hydrogen (the carboxylic acid); an organic or inorganic cation, such as ammonium carboxylate, procaine carboxylate, phenylethylbenzylammonium carboxylate, phenylglycine carboxylate, lysine carboxylate, lithium carboxylate, potassium carboxylate, sodium carboxylate and the like; a carboxy protecting group, such as allyl carboxylate, 4-methoxybenzyl carboxylate, di-(4-methoxy)benzhydryl carboxylate, benzhydryl carboxylate, 2,2,2-trichloroethyl carboxylate, trimethylsilyl carboxylate, (t-butyl)dimethylsilyl carboxylate,'β-(trimethylsilyl)ethyl carboxylate, trityl carboxylate, 4/4',4"-trimethoxytrityl carboxylate, 4-toluenesulfonylethyl carboxylate, and the like; a non-toxic, metabolically-labile ester-forming group, such as methoxymethyl carboxylate, 5-methyl-2-oxo-1,3-dioxolen-4-ylmethyl carboxylate, ethylthiomethyl carboxylate, pivaloyloxymethyl carboxylate, 3-phthalidyl carboxylate, 1-(ethoxycarbonyloxy)eth-1-yl carboxylate, 1-(methylaminocarbonyloxy)eth-1-yl carboxylate and the like.

A preferred group of examples of the carboxyl group —$COOR_8$ occurs when $R_8$ is allyl or t-butyl.

Examples of the group $$-SO_2Y$$

include $C_1$ to $C_6$ alkylsulfonyl groups such as methylsulfonyl, ethylsulfonyl, (t-amyl)sulfonyl and (n-hexyl)sulfonyl, $C_7$ to $C_{12}$ alkylarylsulfonyl groups such as (2-phenyl)propylsulfonyl, benzylsulfonyl, 1-phenyl(n-amyl)sulfonyl and 4-phenyl(n-butyl)sulfonyl; $C_1$ to $C_6$ substituted alkylsulfonyl groups such as cyanomethylsulfonyl, 2-hydroxyethylsulfonyl, 2-nitropropylsulfonyl, 2-carbamoyl(sec-butyl)sulfonyl, 5-chloroamylsulfonyl, 4-carboxyamylsulfonyl, 6-carbamoyloxyhexylsulfonyl, 2-methoxyethylsulfonyl, isopropoxy(t-butyl)sulfonyl, 2-aminoethylsulfonyl, 2,5-dihydroxyamylsulfonyl, 3,3-dibromo(n-butyl)sulfonyl, 3-chloro-2-iodopropylsulfonyl, and 4-acetoxy-6-fluorohexylsulfonyl; $C_1$ to $C_{12}$ substituted alkylarylsulfonyl groups such as 3-(3,4-diiodophenyl)propylsulfonyl, 1-(3-chloro-4-fluorophenyl)ethylsulfonyl, 6-(4-cyanophenyl)hexylsulfonyl, 3-phenyl-1-chloro(sec-butyl)sulfonyl, 2-phenyl-2-hydroxyethylsulfonyl, 5-phenyl-2-hydroxyamylsulfonyl, 2-(3-nitrophenyl)-3-ethoxypropylsulfonyl, 5,6-dihydroxy-2-(4-ethyl-2-hydroxyphenyl)hexylsulfonyl and 5-carbamoyl-3-nitro-4-(2,4-dimethoxyphenyl)amylsulfonyl; phenylsulfonyl, and (substituted phenyl)sulfonyl groups.

Examples of the term (substituted phenyl)sulfonyl include groups such as 4-chlorophenylsulfonyl, 2,6-dichlorophenylsulfonyl, 2,5-dichlorophenylsulfonyl, 3,4-dichlorophenylsulfonyl, 3-chlorophenylsulfonyl, 3-bromophenylsulfonyl, 4-bromophenylsulfonyl, 3,4-dibromophenylsulfonyl, 3-chloro-4-fluorophenylsulfonyl, 2-fluorophenylsulfonyl, 4-hydroxyphenylsulfonyl, 4-(protected hydroxy)phenylsulfonyl, 3-hydroxyphenylsulfonyl, 2,4-dihydroxyphenylsulfonyl, 3- or 4-nitrophenylsulfonyl, 4-cyanophenylsulfonyl, 4-methylphenylsulfonyl, 2,4-dimethylphenylsulfonyl, 2-methylphenylsulfonyl, 4-(iso-propyl)phenylsulfonyl, 4-ethylphenylsulfonyl, 3-(n-propyl)phenylsulfonyl, 2,6-dimethoxyphenylsulfonyl, 4-methoxyphenylsulfonyl, 3-ethoxyphenylsulfonyl, 4-(iso-propoxy)phenylsulfonyl, 4-(t-butoxy)phenylsulfonyl, 3-ethoxy-4-methoxyphenylsulfonyl, 3- or 4-(trifluoromethyl)phenylsulfonyl, 4-carboxyphenylsulfonyl, 2,4-di(protected carboxy)phenylsulfonyl, 3-(protected hydroxymethyl)phenylsulfonyl, 3,4-di(hydroxymethyl)phenylsulfonyl, 2-(aminomethyl)phenylsulfonyl, 2,4-(protected aminomethyl)phenylsulfonyl, 3-(methylsulfonylamino)phenylsulfonyl, 3-methyl-4-hydroxyphenylsulfonyl, 3-chloro-4-hydroxyphenylsulfonyl, 2-methoxy-4-bromophenylsulfonyl, 4-ethyl-2-hydroxyphenylsulfonyl, 3-hydroxy-4-nitrophenylsulfonyl and 2-hydroxy-4-chlorophenylsulfonyl.

A preferred group of examples of the group

—$SO_2Y$ is the methylsulfonyl, phenylsulfonyl, 4-methylphenylsulfonyl and benzylsulfonyl groups, with 4-methylphenylsulfonyl being a more preferred group.

Examples of the compounds of Formula I are listed below in Table I:

substituted phenyl and the other is a group of the formula —$COOR_8$, and especially when Y is phenyl or substituted phenyl. A more preferred group of compounds occurs when $R_2$ is hydrogen, $C_1$ to $C_6$ alkyl, $C_1$ to $C_6$ substituted alkyl, perfluoro $C_2$ to $C_4$ alkyl, $C_7$ to $C_{12}$ alkylaryl, $C_7$ to $C_{12}$ substituted alkylaryl, phenyl, substituted phenyl or cyano; and especially so when $R_1$ is a group of the formula

—$COOR_8$ wherein $R_8$ is a carboxy protecting group.

One series of compounds worthy of note in this group occurs when $R_2$ is hydrogen and especially when $R_8$ is allyl and Y is 4-methylphenyl.

II. Synthesis of the Compounds of Formula I

The 2,3-(dihydro) bicyclic pyrazolidinones of Formula I are the product of a 1,3-dipolar cycloaddition reaction. The cycloaddition reaction is represented below in Scheme 1:

TABLE I
Compounds of the Formula

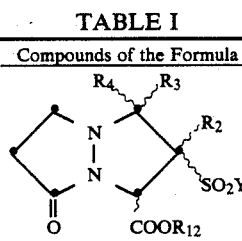

| $R_{12}$ | $R_2$ | $R_3$ | $R_4$ | Y |
| --- | --- | --- | --- | --- |
| allyl | $CH_2Cl$ | H | H | 4-methylphenyl |
| allyl | $CH_2OTHP^1$ | H | H | " |
| allyl | $CH_2OAc$ | H | H | " |
| $pNB^2$ | phenyl | methyl | methyl | methyl |
| $pMB^3$ | H | 3-(trifluoromethyl)phenyl | methyl | 2-chloroethyl |
| benzhydryl | ethyl | phenyl | H | benzyl |
| t-butyl | phenylsulfonyl | 2-(trifluoromethyl)phenyl | H | 4-chlorobenzyl |
| 2,2,2-trichloroethyl | n-propylsulfoxide | Ethyl carboxy | ethyl carboxy | phenyl |
| trimethylsilyl | trifluoromethyl | benzyl | H | 4-methoxyphenyl |
| cinnamyl | 1-methyltetrazol-5-ylthio | H | H | n-propyl |
| acetoxymethyl | formyl | methyl | phenyl | benzyl |
| trityl | acetyl | ethyl | benzyl | 3-phenylpropyl |
| β-(trimethylsilyl)ethyl | perfluorobutyryl | 3-nitrobenzyl | H | 3-phenylbutyl |
| t-amyl | trichloroacetyl | 2,5-dimethylphenyl | methyl | benzyl |
| 2,4,6-trimethylbenzyl | benzoyl | phenyl | 4-methylphenyl | methyl |
| 2-phenylprop-2-yl | 4-nitrobenzoyl | 2,3-dibromopropyl | ethyl | 3-cyanopropyl |
| t-butyldimethyl silyl | 2-phenylacetyl | methyl | methyl | 3-ethylphenyl |
| pentamethylbenzyl | 2-(3-chlorophenyl)-acetyl | H | H | 3-phenyl-2-chloropropyl |
| phenacyl | methyl carboxy | allyl carboxy | H | ethyl |
| 4-nitrobenzyl sulfonylethyl | 2-fluoroethyl carboxy | t-butyl carboxy | t-butyl carboxy | 4-phenylbutyl |
| benzyl | benzyl carboxy | n-propyl | ethyl | hexyl |
| 3,4-dimethoxybenzyl | 4-methylbenzyl carboxy | n-butyl | n-butyl | 1-fluoroethyl |
| benzhydryl | phenyl carboxy | 3-phenyl-2-chloropropyl | H | 2-nitropropyl |
| 1-(trimethylsilylmethyl)prop-1-en-3-yl | 3-nitrophenyl carboxy | H | H | phenyl |
| pivaloyloxymethyl | allyl carboxy | H | H | phenyl |
| ethoxyethyl | ethoxyethyl carboxy | H | H | 4-methylphenyl |
| methylthiomethyl | 1,3,4-thiadiazol-2-ylthiomethyl | H | H | benzyl |

A preferred group of the above examples is when either $R_1$ or $R_2$ is hydrogen, $C_1$ to $C_6$ alkyl, $C_1$ to $C_6$ substituted alkyl, perfluoro $C_2$ to $C_4$ alkyl, $C_7$ to $C_{12}$ alkylaryl, $C_7$ to $C_{12}$ substituted alkylaryl, phenyl or

Scheme 1

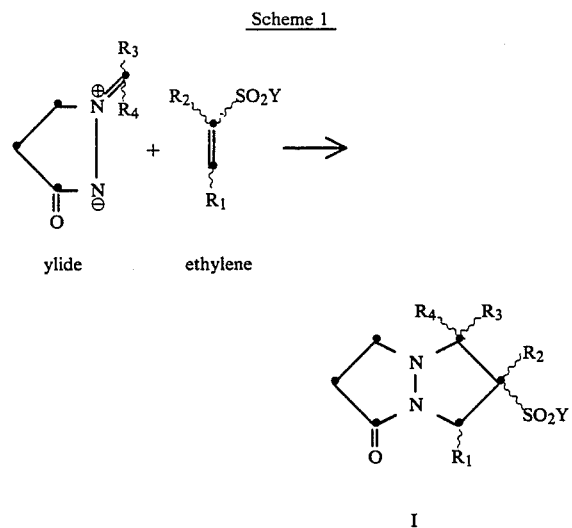

ylide        ethylene

In Scheme 1, $R_1$, $R_2$, $R_3$, $R_4$ and Y are as defined for Formula I. In conjunction with the process represented by the above Scheme 1, it is preferable to derivatize with protecting groups any acidic groups on the ylide, ethylene or bicyclic pyrazolidinone ring system of Formula I represented by $R_1$, $R_2$, $R_3$, $R_4$ or Y. Such acidic groups include the carboxyl group.

The reaction in the above Scheme 1 should be carried out in aprotic solvents. Examples of such solvents are the chlorinated hydrocarbons, the aromatic hydrocarbons and alkyl or aromatic cyano solvents. A preferred solvent for the above reaction is 1,2-dichloroethane.

The temperature for the reaction is not critical. It is preferred that the reaction be carried out between about room temperature to about the reflux temperature of the solvent. A more preferred temperature is approximately the reflux temperature.

The reaction usually requires a period of between about 1 to about 168 hours. The optimal reaction time can be determined by monitoring the progress of the reaction by conventional means such as chromatographic techniques (thin layer chromatography, high performance liquid chromatography, or column chromatography) or spectroscopic methods (such as infrared spectroscopy, nuclear magnetic resonance spectrometry and mass spectrometry), or a combination of the two.

The usual stoichiometry for the reaction is a 1:1 ratio of ylide to ethylene reagent. Of course, an excess of either reagent is permissible. The order of addition of the reagents is not critical.

The regiospecificity of the cycloaddition reaction is such that the 3-(alkyl or aryl sulfonyl) regioisomer is the predominant product. Thus, the cycloaddition reaction is especially useful for placing the substitutent bonded to the sulfonyl-substituted carbon of the ethylene at the 3-position of the bicyclic pyrazolidinone ring.

The compounds of Formula I are converted to unsaturated bicyclic pyrazolidinone antimicrobials (Formula II) according to the elimination reaction set forth below in Scheme 2:

Scheme 2

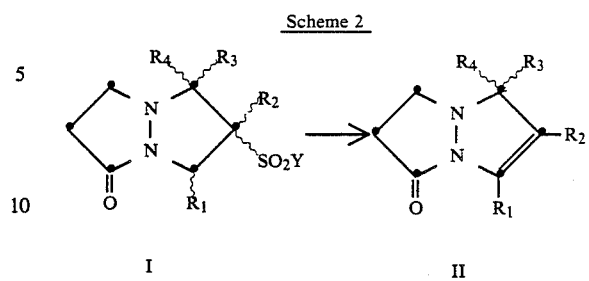

In the above scheme 2, $R_1$, $R_2$, $R_3$, $R_4$ and Y are as defined for Scheme 1. Again, it is preferred that acidic groups at $R_1$, $R_2$, $R_3$, $R_4$ and Y be derivatized with a protecting group. Examples of such acidic groups are the carboxylic acids. The preferred solvent for the elimination reaction is dichloromethane. The elimination is conducted at a temperature from about −78° C. to about room temperature. A non-nucleophilic base, such as 1,8-diazabicyclo[5.4.0]undec-7-ene ("DBU") or 1,5-diazabicyclo[4.3.0]non-5-ene ("DBN"), is used to eliminate the elements of (alkyl or aryl)sulfinic acid. An excess of the non-nucleophilic base in relation to the "saturated system" is normally used.

The pyrazolidinium ylide starting materials for the above cycloaddition reaction are synthesized according to a process depicted below in Scheme 3.

Scheme 3

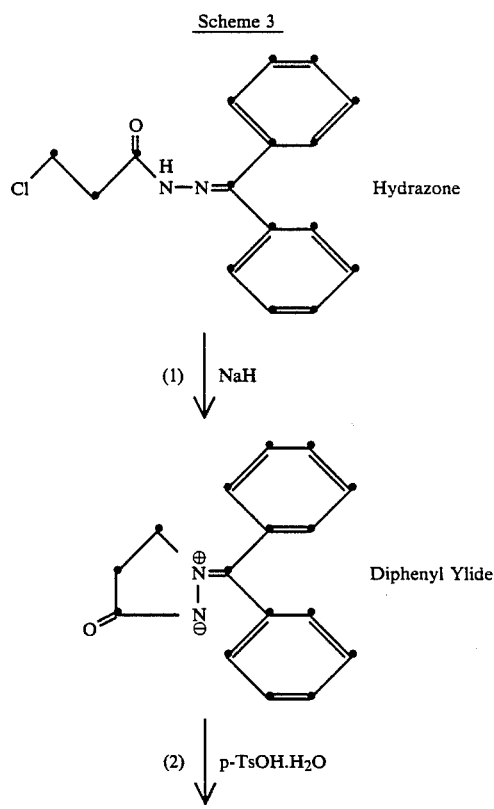

-continued
Scheme 3

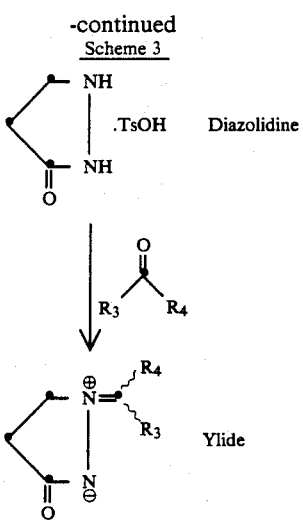

The first step in the synthesis of the ylide starting materials, represented by Reaction 1 in the above Scheme, is a cyclization of the β-chloropropionylhydrazone of benzophenone ("hydrazone") to the 3-oxo-1-(diphenylmethylene)-1,2-pyrazolidinium ylide ("diphenyl ylide") moiety. The cyclization is carried out using sodium hydride in tetrahydrofuran. The reaction solution is stirred at room temperature for 18 hours then at reflux for 2 hours. The synthesis of the hydrazone and the conditions for Reaction 1 are described in E. C. Taylor et al., J. Am. Chem. Soc., 1981, 103, 7743-7752.

The second step, represented in the above Scheme by Reaction 2, is the hydrolysis of the diphenyl ylide to give the 3-oxo-1,2-diazolidine p-toluene sulfonate salt ("diazolidine") compound. The diphenyl ylide is hydrolyzed with one equivalent of p-toluenesulfonic acid monohydrate in dichloromethane, and the hydrolysis is generally complete after 2 hours of stirring at room temperature. The conditions for Reaction 2 are adopted from E. C. Taylor et. al., supra.

The final reaction in the synthesis of the pyrazolidinium ylide starting materials, represented as Reaction 3 in the above scheme, is the condensation of a ketone or aldehyde with a diazolidine to give the pyrazolidinium ylide. The diazolidine and the ketone or aldehyde are combined, either in equimolar amounts or with an excess of the ketone or aldehyde in a solvent chosen from methanol, ethanol or dimethylformamide. Within a minute or two after combining the two reagents in the solvent, excess solid sodium bicarbonate is added and the resultant solution is stirred for 1 or 2 hours at room temperature. As a useful alternative procedure, the ketal of the ketone may be condensed with the diazolidine in the presence of an acid. For example, the diazolidine reagent is combined with acetone dimethyl acetal in methanol and then the solution is treated with d-10 camphorsulfonic acid. The mixture is refluxed for 1.5 hours to give the dimethyl ylide (i.e., $R_3$ and $R_4$ are methyl). When $R_3$ and $R_4$ are different, those skilled in the art will recognize that this final reaction will produce a mixture of E and Z isomers.

The ethylene starting materials in Scheme I are made by methods known in the art. The synthesis of some ethylene starting materials is also described in the Experimental Section below.

Procedures for reactions in the above Scheme 3 are found at Preparations 1 through 3 in the Experimental Section.

The bicyclic pyrazolidinone antimicrobial compounds of Formula II inhibit the growth of certain pathogenic organisms, as demonstrated by standard agar-plate disc-diffusion test. The antimicrobial compounds of Formula II are compounds wherein the various amino, hydroxy and/or carboxy protecting groups have been removed. Representative pathogens which are sensitive to the antibiotic compounds of Formula II include *Staphylococcus aureus* X1, *Escherichia coli* X161, *Escherichia coli* X161M, *Escherichia coli* X580, *Mycobacterium avium* X85 and the like.

The antimicrobial compounds of Formula II are useful for the therapeutic or prophylactic treatment of infections in warm-blooded animals caused by gram-positive, gram-negative and acid-fast bacteria. Alternatively, the compounds can be used as surface disinfectants and as food preservatives.

The antimicrobial compounds can be administered orally, parenterally (e.g. intravenously, intramuscularly, subcutaneously, etc.) or as a topical ointment in treating bacterial infections of warm-blooded animals.

Further aspects of the synthesis and properties of the bicyclic pyrazolidinone antimicrobials of Formula II are found in L. N. Jungheim and S. K. Sigmund, U.S. Ser. No. 06/729,021, now abandoned in favor of U.S. Ser. No. 06/862,906 filed this even date.

The following Examples are provided to further illustrate the invention. It is not intended that the invention be limited in scope by reason of any of the following Preparations or Examples.

In the following Preparations and Examples, the terms nuclear magnetic resonance spectra, mass spectra and infra-red spectra and are abbreviated n.m.r., m.s., and i.r. respectively. In addition, the adsorption maxima listed for the i.r. spectra are only those of interest and not all of the maxima observed. The abbreviation "THF" stands for tetrahydrofuran.

As used in conjunction with the n.m.r. spectra, the abbreviations "s", "d", "br. s", "t", and "m" stand for singlet, doublet, broad singlet, triplet and multiplet, respectively. The abbreviation "J" indicates the coupling constant in Hertz. "DMSO/$d_6$" represents dimethyl sulfoxide where all the protons have been replaced with deuterium.

The n.m.r. spectra were obtained on a Varian Associates EM-390 90 MHz or T-60 60 MHz instrument or on a Jeol FX-90Q 90 MHz instrument. The chemical shifts are expressed in δ values (parts per million downfield from tetramethylsilane). The field desorption mass spectra were taken on a Varian-MAT 731 Spectrometer using carbon dendrite emitters. ElectionImpact Mass Spectra were obtained on a CEC 21-110 instrument from Consolidated Electrodynamics Corporation. Infrared spectra were obtained on a Perkin-Elmer 281 instrument. Thin layer chromatography was carried out on E. Merck silica gel plates.

EXPERIMENTAL SECTION

PREPARATION 1

3-Oxo-1,2-Diazolidine 4-Toluenesulfonate Salt

3-Oxo-1-(diphenylmethylene)-1,2-pyrazolidinium ylide (approximately 5 g, approximately 19 mmol) was dissolved in methylene chloride (100 ml). P-toluenesulfonic acid monohydrate (19 mmol) was added and the resultant solution was stirred at room temperature for 2 hours. The precipitate that formed was collected by filtration and dried in vacuo over 3 Å molecular sieves to give approximately 1.9 g of 3-oxo-1,2-diazolidine p-toluenesulfonate salt: n.m.r. (90 MHz, DMSO-$d_6$); δ 8.8 (br. s, 3), 7.4 (d, 2, J=8), 7.0 (d, 2, J=8), 3.64 (t, 2, J=8), 2.5 (t, 2, J=8), 2.20 (s, 3); i.r. (KBr): 1750 cm$^{-1}$; m.s.: M$^+$=258.

PREPARATION 2

3-Oxo-1-(Methylene)-1,2-Pyrazolidinium Ylide Dimer

3-Oxo-1,2-diazolidine (25.8 g, 0.1 mmol) was dissolved in methanol (200 ml). Aqueous formaldehyde (37%, 10.2 g, 0.125 mmol) was added to the solution followed by the addition of solid sodium bicarbonate (20 g) 1 minute later. The resultant mixture was stirred at room temperature for 45 minutes, filtered and the mother liquors were concentrated in vacuo. The solvent was azeotropically distilled in vacuo with isopropanol (3X, 500 ml) and the final residue was dried in vacuo. The resultant residue was refluxed in methylene chloride (600 ml) for 2 hours, filtered and concentrated in vacuo to give 6.4 g, 5% yield of a colorless solid of 3-oxo-1-(methylene)-1,2-pyrazolidinium ylide dimer: n.m.r. (90 MHz, CDCl$_3$): δ 4.7 (s, 4), 3.46 (t, 4, J=7), 2.56 (t, 4, J=7); i.r. (CHCl$_3$) 1700 cm$^{-1}$; m.s.: M$^+$=196.

PREPARATION 3

3-Oxo-1-(Diphenylmethylene)-1,2-Pyrazolidinium Ylide

Benzophenone β-chloropropionyl hydrazyl (10.04 g, 35 mmol) was dissolved in THF (110 ml). Sodium hydride ((55% oily) 1.52 g, 35 mmol) was added to the solution in portion. The resultant mixture was stirred for 18 hours at room temperature, refluxed for 2 hours, cooled and washed with water. The organic phase was dried over magnesium sulfate, filtered and concentrated in vacuo. The solvent was azeotropically removed by distillation in vacuo with toluene to leave approximately 5 g of a yellow solid of 3-oxo-1-(diphenylmethylene)-1,2-pyrazolidinium ylide: n.m.r. (60 MHz, CDCl3) 8.1–7.1 (m, 10), 4.13 (t, 2, J=8), 3.64 (t, 2, J=8).

EXAMPLE 1

(2R,3S)- And (2S,3R)-2-(Allyl Carboxylate)-3-(P-Toluenesulfonyl)-8-Oxo-1,5-Diazabicyclo[3.3.0]Octane 3-Oxo-1-(methylene)-1,2-pyrazolidinium ylide dimer (0.883 g, 4.5 mmol), allyl 3-(p-toluenesulfonyl)acrylate (2.4 g, 9.0 mmol) and 1,2-dichloroethane (25 ml) are combined under argon and refluxed overnight. The reaction solution is concentrated under reduced pressure and is chromatographed on a silica gel column that is eluted with a solvent gradient of 0 to 50% ethyl acetate in hexane. The chromatography procedure would yield a mixture of 2R,3S and 2S,3R stereoisomers of 2-(allyl carboxylate)-3-(p-toluenesulfonyl)-8-oxo-1,5diazabicyclo[3.3.0]octane.

PREPARATION 4

2-(Allyl Carboxylate)-8-Oxo-1,5-Diazabicyclo[3.3.0]Octa-2-Ene

A mixture of 2R,3S and 2S,3R stereoisomers of 2-(allyl carboxylate)-3-(p-toluenesulfonyl)-8-oxo-1,5-diazabicyclo[3.3.0]-octane (1.094 g, 3.002 mmol) is dissolved in dry methylene chloride (50 ml) and the solution is cooled to −78° C. 1,8-Diazabicyclo[5.4.0]-undec-7-ene ("DBU") (0.548 g, 3.60 mmol) is dissolved in dry methylene chloride (50 ml) and is added to the cooled solution of bicyclic pyrazolidinone. The resultant reaction solution is stirred at −78° C. for 1 hour then warmed slowly to room temperature. The solution is washed with aqueous 0.1N hydrochloric acid, saturated aqueous sodium bicarbonate solution and brine, is dried over magnesium sulfate, filtered and concentrated under reduced pressure. The procedure would yield 2-(allyl carboxylate)-8-oxo-1,5-diazabicyclo[3.3.0]octa-2-ene.

We claim:
1. A compound of the formula:

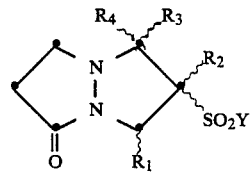

wherein:
either $R_1$ or $R_2$ is hydrogen, $C_1$ to $C_6$ alkyl, $C_1$ to $C_6$ alkyl substituted by one or two halogen, hydroxy, protected hydroxy, amino, protected protected amino, $C_1$ to $C_7$ acyloxy, nitro, carboxy, protected carboxy, carbamoyl, carbamoyloxy, cyano, methylsulfonylamino or $C_1$ to $C_4$ alkoxy groups, or $R_1$ or $R_2$ is a group of the formula

—CX$_3$ wherein X is fluoro, chloro, bromo or iodo;
and the other of $R_1$ or $R_2$ is a group of the formula

—COOR$_8$ wherein $R_8$ is hydrogen, an organic or inorganic cation, a carboxy-protecting group or methoxymethyl, ethoxymethyl, isopropoxymethyl methoxyehtyl ethoxyethyl, propoxyethyl, isopropoxyethyl, 5-methyl-2-oxo-1,3-dioxolen-4-ylmethyl, 5-phenyl-2-oxo-1,3-dioxolen-4-ylmethyl, methylthiomethyl, ethylthiomethyl, isopropylthiomethyl, pivaloyloxymethyl, α-acetoxymethyl, ethoxycarbonyl-1-methyl, α-acetoxyethyl, the 3-phthalidyl or 5,6-dimethylphtalidyl groups, 1-(ethoxycarbonyloxy)eth-1-yl group or the 1-(methylaminocarbonyloxy)eth-1-yl group;
$R_3$ and $R_4$ are the same or different and are hydrogen, $C_1$ to $C_6$ alkyl, $C_1$ to $C_6$ alkyl substituted by one or two halogen, hydroxy, protected hydroxy, amino, protected amino, $C_1$ to $C_7$ acyloxy, nitro, carboxy protected carboxy, carbamoyl, carbamoyloxy, cyano, methylsulfonylamino or $C_1$ to $C_4$ alkoxy groups;
Y is $C_1$ to $C_6$ alkyl, $C_1$ to $C_6$ alkyl substituted by one or two halogen, hydroxy, protected hydroxy, amino, protected amino, $C_1$ to $C_7$ acyloxy, nitro, carboxy protected carboxy, carbamoyl, carbamoyloxy, cyano, methylsulfonylamino or $C_1$ to $C_4$ alkoxy groups, or Y is phenyl, a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl or methylsulfonylamino;

or a pharmceutically acceptable salt thereof.

2. A compound of claim 1, wherein either $R_1$ or $R_2$ is: hydrogen, $C_1$ to $C_6$ alkyl, $C_1$ to $C_6$ alkyl substituted by one or two halogen, hydroxy, protected hydroxy, amino, protected amino, $C_1$ to $C_7$ acyloxy, nitro, carboxy, protected carboxy, carbamoyl, carbamoyloxy, cyano, methylsulfonylamino or $C_1$ to $C_4$ alkoxy groups.

3. A compound of claim 2, wherein Y is phenyl or a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, trifluoromethyl, or methylsulfonylamino.

4. A compound of claim 3, wherein $R_2$ is: hydrogen $C_1$ to $C_6$ alkyl, $C_1$ to $C_6$ alkyl substituted by one or two halogen, hydroxy, protected hydroxy, amino, protected amino, $C_1$ to $C_7$ acyloxy, nitro, carboxy protected carboxy, carbamoyl, carbamoyloxy, cyano, methylsulfonylamino or $C_1$ to $C_4$ alkoxy groups.

5. A compound of claim 4, wherein $R_2$ is hydrogen.

6. A compound of claim 5, wherein $R_8$ is allyl and Y is 4-methylphenyl.

* * * * *